United States Patent [19]

Wurtman

[11] Patent Number: 4,687,763
[45] Date of Patent: Aug. 18, 1987

[54] COMPOSITION AND METHOD FOR INCREASING LEVELS OR RELEASE OF BRAIN SEROTONIN

[75] Inventor: Richard J. Wurtman, Boston, Mass.

[73] Assignee: Massachusetts Institute of Technology, Cambridge, Mass.

[21] Appl. No.: 705,174

[22] Filed: Feb. 25, 1985

[51] Int. Cl.$^4$ .............................................. A61K 31/70
[52] U.S. Cl. ....................................... 514/53; 514/23; 514/54; 514/58; 514/60; 514/415
[58] Field of Search ..................... 514/415, 23, 53, 54, 514/56, 60, 58

[56] References Cited

U.S. PATENT DOCUMENTS 4,210,637  7/1980  Wurtman et al. .................... 536/1.1

Primary Examiner—Johnnie R. Brown
Assistant Examiner—Elli Peselev
Attorney, Agent, or Firm—Paul J. Cook

[57] ABSTRACT

A composition comprising tryptophan and melatonin with or without an insulin-releasing carbohydrate or melatonin and an insulin-releasing carbohydrate is administered to an animal in order to increase the levels or release of brain serotonin.

6 Claims, No Drawings

COMPOSITION AND METHOD FOR INCREASING LEVELS OR RELEASE OF BRAIN SEROTONIN

BACKGROUND OF THE INVENTION

This invention relates to a method and composition for increasing the levels or release of brain serotonin.

At the present time, it is known that brain serotonin levels or release (in neuronal synapses) can be increased by administering to a patient, the amino acid, L-tryptophan while reducing the level of other large neutral amino acids as low as possible so that the other amino acids do not compete with tryptophan for uptake in the brain. It is also known that tryptophan administered in conjunction with a carbohydrate which causes insulin secretion has the effect of potentiating the effect of tryptophan to raise brain serotonin levels by virtue of the fact that the insulin reduces blood plasma levels of competing large neutral amino acids. This is disclosed, for example, in U.S. Pat. No. 4,210,637. It is also known that the levels or release of brain serotonin can be increased by administering, to a patient the hormone, melatonin, which is the hormone normally secreted at night by the human pineal gland. It is believed that the administration of melatonin affects brain serotonin levels or release by a mechanism much different than that of tryptophan, namely, affecting the firing of serotonin-containing neurons.

It would be desirable to provide a means for increasing the release or levels of brain serotonin in a patient in order to facilitate behavioral and physiological functions that depend upon the release of this neurotransmitter. For example, increasing brain serotonin levels facilitates sleep onset and improves the quality of sleep; diminishes appetite, especially for carbohydrates, thereby facilitating weight loss; diminishes sensitivity to painful stimuli; facilitates adaptation to a shift in time zones, thus diminishing "jet-lag"; and is helpful in treating psychiatric disorders including, but not limited to, mania and depression.

SUMMARY OF THE INVENTION

The present invention provides a method and composition for increasing the levels or release of serotonin. The invention is based upon the discovery that a combination of melatonin and tryptophan (either in the presence or absence of a carbohydrate that increases blood insulin levels) or a combination of melatonin and a carbohydrate which increases the blood insulin levels, causes an increase in the levels or release of brain serotonin which is much greater than the additive effects of melatonin and tryptophan (or carbohydrates) individually. The compositions of this invention can be administered alone or in admixture with caffeine or other mild stimulants to override the natural sedating effects that the mixture produces in some people.

DETAILED DESCRIPTION OF SPECIFIC EMBODIMENTS

In accordance with this invention, tryptophan and melatonin either with or without an insulin-reducing carbohydrate or melatonin and an insulin-releasing carbohydrate are administered to a patient. The administration of a carbohydrate that releases insulin decreases the plasma levels of the other neutral amino acids normally found in the plasma such as leucine, isoleucine, tyrosine, phenylalamine and valine. Thus, the carbohydrate causes an increase of the plasma levels of tryptophan in relation to these other amino acids by decreasing the concentration of the other amino acids in the plasma. Both of these effects are cumulative in effecting an increase in brain serotonin levels. In the case where the insulin-releasing carbohydrate is administered together with melatonin, but in the absence of tryptophan, brain serotonin levels are increased by the mechanism of reducing the plasma levels of amino acids that compete with circulating tryptophan for brain uptake. Surprisingly, it has been found that the combination of melatonin and tryptophan cause an increase in the release of brain serotonin levels or in its levels which is far greater than the additive effects of melatonin and tryptophan individually. Furthermore, it has been found that the insulin-releasing carbohydrate serves to potentiate the effects of melatonin in increasing brain serotonin release to a surprising degree.

Representative suitable insulin-releasing carbohydrates useful in this invention include sucrose, dextrose, starch, fructose, invert sugar, dextrins, sugar polymers such as polyose, xylitol and mixtures thereof or the like. The relative proportions of melatonin and an insulin-releasing carbohydrate is weight ratio of melatonin to the carbohydrate of between about 1/100,000 and about 1/50, preferably, between about 1/2500 and about 1/50. When melatonin and tryptophan are utilized in combination, the weight ratio of melatonin to tryptophan is between about 1/10,000 and about 1/50, preferably, between about 1/500 and about 1/50. When melotonin, tryptophan and an insulin-releasing carbohydrate are utilized in combination, the weight ratios of melatonin to tryptophan to the carbohydrate are between 1:150:10,000 and 200:7,000:100,000, preferably, between about 20:700:20,000 and 200:3000:100,000. The compositions of this invention are administered in amounts sufficient to effect increase in brain serotonin levels while not being administered in such large amounts that seriously reduce the brain levels of other neurotransmitters needed for normal functioning such as dopamine, norepinephrine, epinephrine, acetylcholine or the nonessential amino acids. Generally, the compositions of this invention are administered in the amount of between about 0.01 mg/kg and about 3.0 mg/kg of melatonin; 2 mg/kg and 100 mg/kg of tryptophan and 100 mg/kg and 1500 mg/kg of carbohydrate, more usually between about 0.5 mg/kg and about 3.0 mg/kg of melatonin, 10 mg/kg and 100 mg/kg of tryptophan and 150 mg/kg and 1500 mg/kg of carbohydrate. Typical unit dosage forms useful for oral administration range between about 0.5 mg and 200 mg melatonin, 0.15 g and 7.0 g tryptophan and 10 g and 100 g carbohydrate.

The tryptophan can be administered as free amino acids, esters, salts, neutral or synthetic polymers or as constituents of food. The route of administration will generally be oral, for example as a tablet, sustained release capsule, drink, beverage sweetener, wafer, candy, chewing gum. It may be mixed with a mild stimulant such as caffeine for daytime use (to override the sedative effect of tryptophan seen in some people) or used without a mild stimulant.

The release of serontonin from nerve terminals within the brain can be estimated by measuring brain levels of serotonin's chief metabolite, 5-hydroxyindole acetic acid (5-HIAA). A dose of melatonin which has no effect on whole brain 5-HIAA levels when given to rats becomes effective when the animal has been pretreated with tryptophan. The melatonin does not act in itself by enhancing brain tryptophan levels nor by increasing the rise in brain tryptophan caused by giving the supplemental tryptophan. It is believed that the melatonin acts either by accelerating the firing of some serotonin-releasing neurons or by acting directly on the nerve terminals to enhance the release or slow the degradation of the serotonin, i.e., by an entirely different mechanism of action from that associated with tryptophan.

The present invention provides the distinct advantage over the compositions of the prior art. Both of the active compounds, melatonin and tryptophan, are naturally-occurring and present in the human blood stream even without treatment. Both of these compounds, unlike most drugs, are metabolized rapidly in the liver such that tissue levels do not build up and remain elevated long after their administration.

The following example illustrates the present invention and is not intended to limit the same.

EXAMPLE I

This example illustrates that the administration of melatonin and tryptophan to an animal results in a synergistic increase of brain serotonin levels.

Twenty-four male Sprague-Dawlet rats weighing 200 g were housed in single cages in light-proof cubicles. After acclimating to this environmnet and having ad libitum access to a stock diet (Charles River Rat, Mouse and Hamster Maintenance Formula) for one week at 22° C. and being given access to water ad libitum and being exposed to light (Vita-Lite; DuroTest Mfg. Co.) between midnight and noon, animals were, on the test day, divided into four groups at 8 AM and deprived of food. At 10 AM, half of the animals (groups 1 and 4) received placebo (2% ethanol in saline; 0.1 ml/200 g body weight) and half received melatonin (1 mg/kg; also as 0.1 ml/200 g body weight) intraperitoneally. One hour later rats in groups 1 and 2 received placebo (saline) while those in groups 3 and 4 received L-tryptophan (100 mg/kg, in the same volume as the saline; 0.1 mg/200 g body weight). One hour after the second injections, animals were sacrificed. Brains were assayed fluorimetrically for serotonin, 5 HIAA and tryptophan.

|  | placebo & placebo (1) | mel. & placebo (2) | placebo & trypt. (3) | mel. & trypt. (4) |
|---|---|---|---|---|
| 5-HIAA | (nanograms per gram of brain) | | | |
|  | $359 \pm 13^a$ | $339 \pm 13^a$ | $581 \pm 18^b$ | $675 \pm 26^c$ |
| Tryptophan | (micrograms per gram of brain) | | | |
|  | $4.65 \pm .16^a$ | $4.73 \pm .15^a$ | $30.4 \pm 1.8^b$ | $33.4 \pm 2.1^b$ |

Numbers in a row with differing letter subscripts (a,b,c) differ from each other significantly (P less than 0.05; analysis of variance; Neumann-Keuls test).

These observations show that a dose of melatonin that failed to increase serotonin release when given with the tryptophan placebo (i.e., 359 vs 339 ng), was able to increase serotonin release in animals also receiving tryptophan (675 vs 581 ng).

I claim:

1. A composition which, when administered to an animal, increases the release or levels of brain serotonin which consists essentially of tryptophan in an amount effective to increase brain serotonin levels and melatonin.

2. The composition of claim 1 which includes a carbohydrate in an amount effective to cause insulin to be released in the animal.

3. A composition which, when administered to an animal, increases brain serotonin levels which consists essentially of melatonin and a carbohydrate in an amount effective to cause insulin to be released in the animal.

4. The composition of any one of claims 2 or 3 wherein the carbohydrate is a sugar.

5. The composition of any one of claims 2 or 3 wherein the carbohydrate is sucrose.

6. The composition of any one of claims 1, 2 or 3 which includes caffeine.

* * * * *